(12) United States Patent
Schense et al.

(10) Patent No.: US 8,309,518 B2
(45) Date of Patent: Nov. 13, 2012

(54) DRUG DELIVERY MATRICES TO ENHANCE WOUND HEALING

(75) Inventors: Jason C. Schense, Zurich (CH); Hugo Schmoekel, Zurich (CH); Jeffrey A. Hubbell, Epalinges (CH); Franz Weber, Zurich (CH)

(73) Assignees: Eidgenossische Technische Hochschule Zurich, Zurich (CH); Universitat Zurich, Zurich (CH)

( * ) Notice: Subject to any disclaimer, the term of this patent is extended or adjusted under 35 U.S.C. 154(b) by 0 days.

(21) Appl. No.: 12/845,354

(22) Filed: Jul. 28, 2010

(65) Prior Publication Data

US 2010/0291215 A1 Nov. 18, 2010

Related U.S. Application Data

(63) Continuation of application No. 11/739,607, filed on Apr. 24, 2007, which is a continuation of application No. 10/132,619, filed on Apr. 25, 2002, now abandoned.

(60) Provisional application No. 60/286,307, filed on Apr. 25, 2001.

(51) Int. Cl.
*A61K 38/18* (2006.01)
*A61K 38/36* (2006.01)
*C07K 14/495* (2006.01)
*C07K 14/51* (2006.01)

(52) U.S. Cl. ........ 514/8.8; 514/8.9; 514/13.6; 514/16.7; 530/382

(58) Field of Classification Search .................. None
See application file for complete search history.

(56) References Cited

U.S. PATENT DOCUMENTS

| | | | |
|---|---|---|---|
| 5,206,023 | A | 4/1993 | Hunziker |
| 5,606,031 | A | 2/1997 | Lile et al. |
| 5,770,194 | A | 6/1998 | Edwardson et al. |
| 6,117,425 | A | 9/2000 | MacPhee et al. |
| 6,150,328 | A | 11/2000 | Wang et al. |
| 6,197,325 | B1 | 3/2001 | MacPhee et al. |
| 6,221,854 | B1 | 4/2001 | Radomsky |
| 6,331,422 | B1 | 12/2001 | Hubbell et al. |
| 6,723,344 | B2 | 4/2004 | Sakiyama-Elbert et al. |
| 7,413,739 | B2 | 8/2008 | Hubbell et al. |

FOREIGN PATENT DOCUMENTS

| | | |
|---|---|---|
| WO | WO 89/09787 | 10/1989 |
| WO | WO 90/09783 | 9/1990 |
| WO | 0 530 804 | 3/1993 |
| WO | WO 98/31788 | 7/1998 |
| WO | WO 00/44808 | 8/2000 |
| WO | WO 00/64481 | 11/2000 |

OTHER PUBLICATIONS

Ruppert et al. Human bone morphogenetic protein 2 contains a heparin-binding site which modifies its biological activity. Eur J Biochem. Apr. 1, 1996;237(1):295-302.*

Chen, et al., "The Golgi sialoglycoprotein MG160, expressed in Pichia pastoris, does not require complex carbohydrates and sialic acid for secretion and basic fibroblast growth factor binding," *Biochem Biophys Res Common* 234(1): 68-72 (1997).
Herbert, et al., "Effects of fibrinolysis on neurite growth from dorsal root ganglia cultured in two- and three-dimensional fibrin gels," *J Compar Neuro* 365(3): 380-391 (1996).
Hildebrand, et. al., "The effects of platelet-derived growth factor-BB on healing of the rabbit medial collateral ligament. An in vivo study," *Am J Sports Med* 26(4): 549-554 (1998).
Hoppe, et al., "Preparation of biologically active platelet-derived growth factor type BB from a fusion protein expressed in *Escherichia coli*," *Biochemistry* 28(7): 2956-2960 (1989).
Hoppe, et al., "Preparation of biologically active platelet-derived growth factor isoforms AA and AB. Preferential formation of AB heterodimers," *Eur J Biochem* 187(1): 207-214 (1990).
Isaacs, "Cystine knots", *Curr. Opin. Struct. Biol.*, 5(3):391-5 (1995).
Jin et. al., "Effects of geometry of hydroxyapatite as a cell substratum in BMP-induced ectopic bone formation," *J Biomed Mat Res* 52, 491-499 (2000).
Lasa, et al., "Delivery of demineralized bone powder by fibrin sealant," *Plast. Reconstr. Surg.* 96(6):1409-17 (1995).
Lin, et al., "Purification and initial characterization of rat B49 glial cell line-derived neurotrophic factor," *J Neurochem* 63(2): 758-768 (1994).
Miyazono, et al., "Divergence and convergence of TGF-beta/BMP signaling", *J. Cell Physiol.*, 187(3):265-76 (2001).
Pandit, et al., "Fibrin scaffold as an effective vehicle for the delivery of acidic fibroblast growth factor (FGF-1)," *J Biomater Appl* 14(3): 229-242 (2000).
Pineda-Lucena, et al., "Three-dimensional structure of acidic fibroblast growth factor in solution: effects of binding to a heparin functional analog," *J Mol Biol* 264(1): 162-178 (1996).
Pisano, et al., "Cross-link in fibrin polymerized by factor 13: epsilon-(gamma-glutamyl)lysine," *Science* 160(3830): 892-893 (1968).
Pittman, et al., "Degradation of extracellular matrix by neuronal proteases," *Dev Neuro* 11(4-5): 361-375 (1989).
Quirinia, et al., "The effect of recombinant basic fibroblast growth factor (bFGF) in fibrin adhesive vehicle on the healing of ischaemic and normal incisional skin wounds," *Scand J Plast Reconstr Surg Hand Surg* 32(1): 9-18 (1998).

(Continued)

*Primary Examiner* — David Romeo
(74) *Attorney, Agent, or Firm* — Pabst Patent Group LLP

(57) ABSTRACT

Bioactive molecules are entrapped within a matrix for the controlled delivery of these compounds for therapeutic healing applications. The matrix may be formed of natural or synthetic compounds. The primary method of entrapment of the bioactive molecule is through precipitation of the bioactive molecule during gelation of the matrix, either in vitro or in vivo. The bioactive molecule may be modified to reduce its effective solubility in the matrix to retain it more effectively within the matrix, such as through the deglycosylation of members within the cystine knot growth factor superfamily and particularly within the TGFβ superfamily. The matrix may be modified to include sites with binding affinity for different bioactive molecules, for example, for heparin binding.

14 Claims, 5 Drawing Sheets

OTHER PUBLICATIONS

Rajan, et al., "Characterization of recombinant human interleukin 4 receptor from CHO cells: role of N-linked oligosaccharides," *Biochem Biophys Res Commun* 206(2): 694-702 (1995).

Robello, et al., "Delayed and nonunion fractures," *Semin Vet Med Surg (Small Anim)* 7(1): 98-104 (1992).

Sampath, et al., "Bovine osteogenic protein is composed of dimers of OP-1 and BMP-2A, two members of the transforming growth factor-beta superfamily", *J. Biol. Chem.*, 265(22)13198-205 (1990).

Sawhney, et al., "Bioerodible Hydrogels Based on Photopolymerized Poly(ethylene glycol)-co-poly($\alpha$-hydroxy acid) Diacrylate Macromers", *Macromolecules*, 26:581-587 (1993).

Schense, et al., "Cross-linking exogenous bifunctional peptides into fibrin gels with factor XIIIa," *Bioconj Chem* 10(1): 75-81 (1999).

Schmitz, et al., "The critical size defect as an experimental model for craniomandibulofacial nonunions," *Clin Orthop* 205: 299-308 (1986).

Sierra, "Fibrin sealant adhesive systems: a review of their chemistry, material properties and clinical applications," *J Biomater Appl* 7(4): 309-352 (1993).

Tamaki, et al., "Cross-linking of alpha 2-plasmin inhibitor to fibrin catalyzed by activated fibrin-stabilizing factor," *J Biol Chem* 257(24): 14767-14772 (1982).

Tams, et al., "Adapting protein solubility by glycosylation. N-glycosylation mutants of *Coprinus cinereus* peroxidase in salt and organic solutions," *Biochem Biophys Acta* 1432(2): 214-221 (1999).

Urist, et al., "Solubilized and insolubilized bone morphogenetic protein," *Proc Natl Acad Sci U.S.A.* 76(4): 1828-1832 (1979).

Wozney, "Bone morphogenetic proteins," *Prog Growth Factor Res* 1(4): 267-280 (1989).

Wozney, et al., "Growth factors influencing bone development," *J Cell Sci Suppl* 13: 149-156 (1990).

* cited by examiner

DRUG DELIVERY MATRICES TO ENHANCE WOUND HEALING

CROSS-REFERENCE TO RELATED APPLICATIONS

This application is a continuation of pending prior application U.S. Ser. No. 11/739,607 filed Apr. 24, 2007, entitled "Drug Delivery Matrices to Enhance Wound Healing," by Jason Schense, Hugo Schmoekel, Jeffrey A. Hubbell and Franz Weber, which is a continuation application of U.S. Ser. No. 10/132,619 filed on Apr. 25, 2002, which claims priority to U.S. Provisional Application No. 60/286,307 filed Apr. 25, 2001, all of which are herein incorporated in their entirety by reference.

BACKGROUND OF THE INVENTION

This invention is generally in the field of drug delivery and more specifically in the area of fibrin and synthetic matrices to enhance wound healing.

Fibrin matrices are present naturally in the body and serve as the initial matrix for wound healing. When an injury occurs to tissue, blood vessels are compromised, allowing the precursor molecule, fibrinogen, to invade the wound. The fibrinogen is then enzymatically cleaved and self-catalyzed into a loosely formed gel. The gel is then covalently crosslinked through the action of the transglutaminase, factor XIIIa, resulting in a stable matrix. Pisano, Finlayson and Peyton, *Science,* 160, 892-893 (1968).

In vivo, the final fibrin matrix includes various proteins in addition to fibrinogen, such as serum proteins present during the coagulation process, for example fibronectin and α2-plasmin inhibitor. Factor XIIIa can covalently crosslink these serum proteins to the fibrin matrix, which can then add additional bioactivities to the matrix that can modify the ability of cells to infiltrate and degrade the matrix. Tamaki and Aoki, *J Biol Chem,* 257, 14767-14772 (1982). These matrices also contain many blood cells, which become entrapped inside the matrix during coagulation, further modifying the biochemical character of the matrix. One major cell type is the platelet, a cell rich with natural supplies of potentially therapeutic growth factors.

One key advantage of fibrin is that it is a matrix that is strongly conductive for cells, allowing them to easily infiltrate the wound site. The process employed involves two key features. First, the matrix contains adhesion sites, allowing the cells to attach and migrate into the gel. Additionally, the matrix is responsive to cell-derived proteolytic activity. This allows the matrix to be degraded locally, allowing the cells to migrate into the matrix uninhibited but preventing global degradation of the matrix. Herbert, Bittner and Hubbell, *J Compar Neuro,* 365, 380-391 (1996); Pittman and Buettner, *Dev Neuro,* 11, 361-375 (1989). Therefore, the natural matrix remains at the site of injury until it is infiltrated by cells, at which time it is degraded during this process leading to regenerated tissue.

The natural healing process is sometimes inadequate, such as when this general healing response fails to lead to regeneration of functional specialized tissue. See for example, Robello G T and Aron D N, *Semin Vet Med Surg (Small Anim),* 7, 98-104 (1992). Therefore, there is a need for a means to induce formation of complete, functional regenerated tissue, especially regenerated specialized tissue.

Many bioactive molecules, including growth factors, peptides, and other assorted molecules, have been discovered which can affect tissue regeneration. Schense and Hubbell, *Bioconj Chem,* 10, 75-81 (1999). Previous work has shown that growth factors can be precipitated within a fibrin matrix. MacPhee, Druhan et al., 76 (1995); U.S. Pat. Nos. 6,117,425 and 6,197,325 to MacFee, et al. However, these investigators have not recognized the strong advantages of working with non-glycosylated growth factors, and especially non-glycosylated members of the cystine knot growth factor superfamily, in particular of the TGFβ superfamily.

Growth factors play an important role in wound healing, and are often naturally present at the site of injury. However if growth factors are applied to the body in high concentrations, adverse effects are likely to be observed. For example, if the retention mechanism of bone morphogenetic protein (BMP) in a matrix is not optimized, i.e. if the BMP simply diffuses from the matrix within the first hours, high doses of BMP in the matrix are necessary to cause a local response at the site of injury. As a result most of the BMP circulates freely in the body and ectopic bone formation may occur. It is therefore necessary to keep the freely circulating concentration of the growth factor as low as possible, while maintaining a concentration which is sufficiently high locally so that the desired therapeutic response is triggered at the site of injury. Some growth factor receptors must be occupied for at least 12 hours to produce a maximal biologically effect. Therefore, a prolonged contact caused by a small but constant stream of growth factor near the site of need is very favorable for a healing response. At the same constant release rate, as the initial concentration of growth factor retained in the matrix increases, the time period for release from the matrix increases.

Therefore it is an object of the present invention to increase the retainable concentration of bioactive molecules, in particular growth factors, in a matrix.

A further object of the present invention is to provide a method to decrease the solubility of a growth factor in a matrix made from fibrin or synthetic polymers.

It is still a further object of the present invention to provide compositions and methods for making compositions to improve wound healing.

BRIEF SUMMARY OF THE INVENTION

Bioactive molecules are entrapped within a matrix for the controlled delivery of these compounds for therapeutic healing applications. The matrix may be formed of natural or synthetic compounds. The primary method of entrapment of the bioactive molecule is through precipitation of the bioactive molecule during gelation of the matrix, either in vitro or in vivo. The bioactive molecule may be modified to reduce its effective solubility in the matrix to retain it more effectively within the matrix, such as through the deglycosylation of members within the cystine knot growth factor superfamily and particularly within the TGF superfamily. The matrix may be modified to include sites with binding affinity for different bioactive molecules, for example, for heparin binding. When these different bioactive molecules are added to the matrix, the bioactive molecules are bound to the matrix both by precipitation within the matrix and by binding to the sites in the matrix, thereby providing enhanced controlled delivery to a patient.

BRIEF DESCRIPTION OF THE DRAWINGS

In FIG. 3A, the fibrin gels were polymerized with 10 (△), 20 (□), 100 (◇) and 200 (○) µg/mL of non-glycosylated rh-BMP-2 present during polymerization of the gel and the percent of rh-BMP-2 remaining in the gel was determined after 10, 20, 30, 40, and 50 wash volumes in PBS. In FIG. 3B, the retention in fibrin gels with 20 µg/mL of prokaryotic rh-BMP-2 (□), 20 mg/mL of glycosylated rh-BMP-2 derived from CHO cells (◇) and 20 µg/mL of rh-BMP-2 premixed with equimolar heparin (○) was analyzed as well. Mean values and standard deviations are shown in each figure.

In FIG. 4 A, non-glycosylated rh-BMP-2 was mixed within the fibrin gel in concentrations of 0 (column I), 1 (column II), 5 (column III), and 20 (column IV) µg/mL. Additionally in FIG. 4B, fibrin gel (column I), fibrin gel mixed with the same heparin level (column V), fibrin gel with 1 µg/mL non-glycosylated rh-BMP-2 (column II), fibrin gel with 1.0 µg/mL glycosylated rh-BMP-2 with a transglutaminase domain to covalently link it to the fibrin gel (as described in U.S. Pat. No. 6,331,422 to Hubbell et al.), fibrin gel with 1 µg/mL non-glycosylated rh-BMP-2 premixed with an equimolar amount of heparin (column VII), and fibrin gel with 1 µg/mL glycosylated rh-BMP-2 (column VIII) were tested. The average area of the defect filled with calcified tissue after 21 days of healing with standard deviations is depicted in these figures.

DETAILED DESCRIPTION OF THE INVENTION

Definitions

Figure 1A:
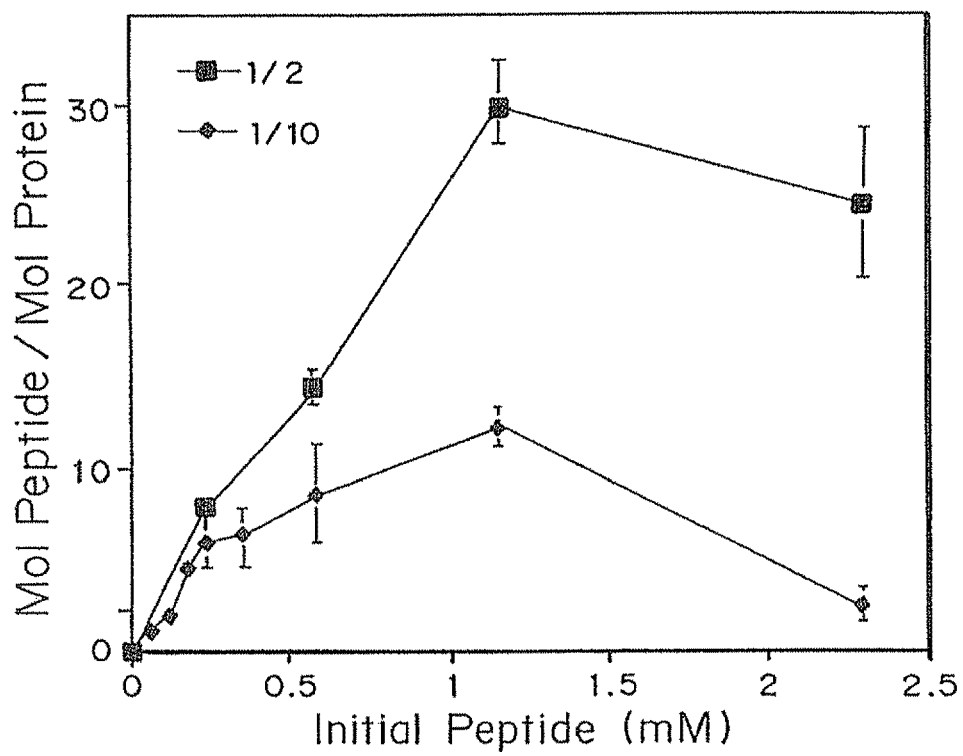
FIGS. 1A and 1B are graphs measuring the incorporation of a factor XIIIa substrate peptide into fibrin. Fibrin gels were synthesized at 8 mg/mL from pre-diluted TISSUCOL™ Kits (Baxter) (a fibrin sealant containing fibrinogen, aprotinin, thrombin, and CaCl$_2$) (FIG. 1A) which were diluted by a factor of 2 (■) and 10 (♦) or from purified fibrinogen either with (♦) or without (■) 1 U/mL of exogenous factor XIIIa added to the prepolymerization mixture (FIG. 1B).

As defined hereing, a bioactive factor is "precipitated" if the concentration of bioactive factor exceeds the concentration limit that is soluble in the respective vehicle at a predefined pH and temperature. Alternatively, precipitation also can encompass retention due to any physical interaction between the bioactive molecule and the matrix, i.e. adsorption, electrostatic forces, affinity precipitation, co-precipitation etc. The terms "entrapment", "inclusion" and "precipitation" are used synonymously as ways to achieve retention.

"Matrix" means a three-dimensional network which can act as a scaffold for cell ingrowth and for bioactive molecules over a certain period of time.

"Deglycosylated bioactive molecules" means bioactive molecules which are not glycosolated, though, when found in nature, they are glycosylated at one or more sites of the molecule. In these molecules, the glycosylation has been removed from the molecule by chemical or enzymatic methods or by producing it as a non-glycosylated molecule. A "deglycosylated growth factor" is a growth factor that can be glycosylated when expressed in a eukaryotic cell and where the polysaccharide sequence or glycosaminoglycans has been either clipped off after expression or the method of expression is such that the growth factor is not glycosylated. The latter happens for example if the growth factor is expressed in a prokaryotic cell. The terms "deglycosylated", "non-glycosylated" and "not glycosylated" are used synonymously herein.

"Retention" means that at least 10% of the initially applied concentration of bioactive molecule, preferably at least 60% and even more preferably at least 80%, is still present in the matrix after 10 wash volumes. Ten wash volumes refers to placing the matrix in a solution resulting in a volume ratio of 1 part matrix to 10 parts of phosphate buffered saline (PBS 0.01M; pH 7.4) for at least 12 hours at 37° C. Retention can be achieved, for example, by precipitation of the bioactive molecule. "Retainable concentration" means that percentage of the initial concentration which is retained according to the manner described above.

The terms "release in a controlled manner", "controlled release" and "prolonged release" have the same meaning and express the result of retention. Controlled release is due not only to slow and steady disintegration of the growth factor and its subsequent diffusion from the matrix, but is also due to the disintegration and enzymatic cleavage of the matrix.

"Gelation" means the formation of a three-dimensional network and thus the transition from a liquid composition to a viscous composition. The terms "gel" and "matrix" are used synonymously throughout the application. An in situ formation of the gel or matrix is due to the transition from a liquid state to a solid state at the site of application in the body. "Hydrogel" means a class of polymeric materials which are extensively swollen in an aqueous medium, but which do not dissolve in water.

"Michael addition" or "Michael-type addition reaction" is the 1,4 addition reaction of a nucleophile to a conjugate unsaturated system under basic conditions. The addition mechanism can be purely polar, or proceed through one or more radical-like intermediate state(s). Lewis bases or appropriately designed hydrogen bonding species can act as catalysts. The term "conjugation" can refer both to alternation of carbon-carbon, carbon-heteroatom or heteroatom-heteroatom multiple bonds with single bonds, or to the linking of a functional group to a macromolecule, such as a synthetic polymer or a protein. Double bonds spaced by a CH or CH$_2$ unit are referred to as homoconjugated double bonds.

Michael-type addition to conjugated unsaturated groups can take place in substantially quantitative yields at physiological temperatures, in particular at body temperature, but also at lower and higher temperatures. These reactions take place in mild conditions with a wide variety of nucleophiles, like amines and thiols.

The reaction as described herein is self-selective. Thus, the first precursor component of the reaction reacts much faster with the second precursor component of the reaction than with other compounds present in the mixture at the site of the reaction; and the second precursor component reacts much faster with the first precursor component than with other compounds present in the mixture at the site of the reaction. As used herein, a nucleophile preferentially binds to a conjugated unsaturated group, rather than to other biological compounds, and a conjugated unsaturated group preferentially binds to a nucleophile rather than to other biological compounds.

"Polymeric network" means a structure in which substantially all of the monomers, oligomers or polymers present in the structure are bound by intermolecular covalent linkages through their available functional groups to result in one large molecule.

"In situ formation" refers to formation at a physiological temperature and at the site of injection in the body. This term is typically used to describe the formation of covalent linkages between precursor molecules, which are substantially not crosslinked prior to and at the time of injection.

"Polymerization" and "cross-linking" are used to indicate the linking of multiple precursor molecules, which results in a substantial increase in the molecular weight of the resulting molecule. "Cross-linking" further indicates branching, typically to yield a polymer network.

"Functionalize" means to modify in a manner that results in the attachment of a functional group or moiety. For example, a molecule may be functionalized by the introduction of a molecule which makes the molecule a strong nucleophile or a conjugated unsaturation. Preferably a molecule, for example PEG, is functionalized to become a thiol, amine, acrylate, or quinone.

"Functionality" refers to the number of reactive sites on a molecule. As used herein, the functionality of a strong nucleophile and a conjugated unsaturation will each be at least two. Mixing two components, for example a strong nucleophile and a conjugated unsaturation, with functionalities of two each, will result in a linear polymeric biomaterial. If at least one component has a functionality that is greater than two, upon mixing a cross-linked biomaterial will be formed.

"Regenerate" means to grow back a portion or all of a tissue. For example, methods of regenerating bone following trauma, tumor removal, or spinal fusion, or for regenerating skin to aid in the healing of diabetic foot ulcers, pressure sores, and venous insufficiency are described herein. Tissues which may be regenerated include, but are not limited to, skin, bone, nerve, blood vessel, and cartilage tissue.

As used herein, "peptide" and "protein" are differentiated by their chain length. "Peptide" means polyaminoacids containing up to 30 amino acids, preferably from about 10 to 20 amino acids. "Proteins" are polyaminoacids containing more than 30 amino acids.

I. Compositions

Compositions are formed of a natural or synthetic matrix and a bioactive molecule, in particular a growth factor, which can be administered to a patient to improve wound healing. The bioactive compound is released in a controlled manner from the matrix. The bioactive molecule is preferably a deglycosylated member of the cystine knot growth factor superfamily, most preferably a non-glycosylated member of the TGFβ superfamily.

A. Matrix

The matrices may be biodegradable or nondegradable. The matrices may be made of synthetic polymers, natural polymers, oligomers, or monomers. Synthetic polymers, oligomers, and monomers include those derived from polyalkyleneoxide precursor molecules, such as poly(ethylene oxide) (PEO), poly(ethylene glycol) (PEG) and copolymers with poly(propylene oxide) (PEG-co-PPO), poly(vinyl alcohol) (PVA), poly(vinylpyrrolidone) (PVP), poly(ethyloxazoline) (PEOX), polyaminoacids, and pseudopolyamino acids, and copolymers of these polymers. Sawhney A S, Pathak C P and Hubbell J A, *Macromolecules,* 26, 581-587 (1993). Copolymers may also be formed with other water-soluble polymers or water insoluble polymers, provided that the conjugate is water soluble. An example of a water-soluble conjugate is a block copolymer of polyethylene glycol and polypropylene oxide, commercially available as a Pluronic™ surfactant (BASF).

Natural polymers, oligomers and monomers include proteins, such as fibrinogen, fibrin, gelatin, collagen, elastin, zein, and albumin, whether produced from natural or recombinant sources, and polysaccharides, such as agarose, alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageen. These polymers are merely exemplary of the types of matrices that can be utilized and are not intended to represent all the matrices within which entrapment is possible.

1. Fibrin Matrices

Due to its natural role in healing and cell infiltration conductive abilities, fibrin is a preferred choice for making a matrix. In a preferred embodiment, the matrix is a fibrin gel, created from any source of fibrinogen. When mixed with the proper amount of thrombin, calcium and bioactive molecule, a fibrin gel can be created at physiological conditions, which means at conditions as found in humans and animals. However, fibrin gel formation can also occur outside the body in the presence of thrombin and calcium and mainly depends on temperature and pH. The fibrin gel can be formed outside the body at a temperature range of between 25° C. to 40° C. and a pH range of between 7 to 8. If the bioactive molecule is not soluble at these conditions, it will precipitate during polymerization and become entrapped within the matrix.

As an additional attribute, many forms of fibrin are available for use as a matrix. Fibrin gels can be synthesized from autologous plasma, cryoprecipitated plasma (e.g. fibrin glue kits, which are available commercially), fibrinogen purified from plasma, and recombinant fibrinogen and factor XIIIa. Each of these materials provides a fundamentally similar matrix, with small variations in the biochemical compositions. Sierra D H, *J Biomater Appl,* 7, 309-352 (1993). Similarities between these materials exist both in specific enzymatic bioactivity and general healing responses.

2. Synthetic Matrices

Synthetic matrices are known in tissue regeneration and wound healing. These include macroporous sponges of degradable polymers such as polylactic acid and its copolymers as well as hydrogel matrices based on water-soluble polymers such as PEG.

a. Polyethylene Glycol Multi-acceptor Precursor Component

In a preferred embodiment, PEG is a precursor molecule for the formation of an enzymatically degradable matrix. PEG is functionalized with chemically reactive groups, such as acceptor groups in the form of conjugated unsaturated bonds, including acrylates, vinyl sulfones and acrylamides, for Michael-type addition reactions. In a preferred embodiment, the PEG is a four-armed PEG with a weight average molecular weight of 15 to 25,000 kDa. The PEG precursors are in solution and are mixed with a second precursor molecule, such as peptides.

b. Peptide Nucleophilic Precursor Component

The peptides are in solution and contain two or more reduced cystine residues (nucleophilic thiol groups), with protease substrate sites intervening between the cystine sites.

Peptides with multiple cystines are described in WO 00/44808 to Elbert et al., published Aug. 3, 2000, herein incorporated by reference. Under basic conditions, a gel forms rapidly by a Michael-type addition reaction between the multi-thiol component (the second precursor) and the multi-acceptor component (the first precursor, a functionalized PEG), so long as the sum of the functionality of the multi-acceptor (the number of Michael acceptor groups (m) per molecule) and the functionality of the multi-thiol (number of thiol groups (n) per molecule) is greater than 5. The Michael addition between the thiol and the acceptor groups works from pH 6.5 up to very basic conditions at a wide variety of temperatures. However, when the precursor components are injected into the body for an in situ formation of the matrix, the pH must be appropriate for the body. Therefore in a preferred embodiment, the pH is between 7 and 8. A preferred temperature range is between 25° C. to 40° C. when the gel is formed outside the body. Inside the body, the gel is formed at body temperature.

When the peptide is designed to be a substrate for plasmin or a matrix metalloproteinase, the resulting synthetic gels degrade in response to the enzymatic matrix remodeling influence of cells.

c. Non-peptide Nucleophilic Precursor Component

The multi-thiol, i.e. the nucleophilic precursor component, does not have to be a peptide. For example, if the matrix does not have to be enzymatically degradable, the nucleophilic precursor component can be a PEG. Optionally, the gel may further comprise cell attachment sites, such as RGD sequences, covalently bound to the matrix to promote ingrowth and attachment of cells into the matrix. The cell attachment site can be bound to the matrix by Michael addition reaction. For the Michael addition reaction, the RGD is modified such that it contains free thiol or cystine groups for reaction with the conjugated unsaturated bond.

B. Bioactive Molecules

The matrices can be further modified by including bioactive molecules, often derived from development, to enhance the regeneration of the wounded tissue. Pandit et al., *J Biomater Appl*, 14, 229-42 (2000); Hildebrand et. al., *Am J Sports Med*, 26, 549-54 (1998); Quirinia A, *Scand J Plast Reconstr Surg Hand Surg*, 32, 9-18 (1998).

The type of molecule that is entrapped can be any of a large list of possible bioactive molecules, including growth factors, peptides, enzymes, protease inhibitors, antibiotics, synthetic homologues and other assorted molecules. Preferred bioactive molecules have reduced solubility at physiological pHs.

1. Growth Factors

Growth factors are particularly useful because they provide a well-characterized chemical entity that has been shown to play an important role in wound healing, and are often naturally present at the site of injury. Additionally, growth factors are pluripotent molecules, allowing them to activate many different cell types and induce a complicated healing response.

The crystal structure of members of the cystine knot growth factor superfamily has been reported as having unusual folds, involving intramolecular disulphide bridges. In transforming growth factor-beta 2 (TGFβ2), platelet derived growth factor (PDGF), nerve growth factor (NGF), and human chorionic ganodotropin (hCG), six conserved cystines (I to IV in sequence order) form three disulphide links arranged in a knot-like topology. Cystines [II to V] and [III to VI] form a ring of eight amino acids through which the remaining disulphide bond (Cys [I to IV]) penetrates the molecule. This topology differs from the structural class of inhibitor like cystine knots in which Cys [III to IV] penetrates a macrocyclic ring formed by Cys [I to IV] and Cys [II to V]. Thus cystine knots fall into two structural classes: growth factor-type and inhibitor-like cystine knots. Members of the cystine knot growth factor superfamily include the platelet derived growth factor (PDGF) superfamily, the transforming growth factor beta (TGFβ) superfamily and the glycoproteins alpha family. Examples of individual growth factors are BMPs, PDGFs, TGF betas. Not all of the growth factors are glycosylated when expressed by eukaryotic cells; for example, TGF beta 1, 2, and 3 are never glycosylated, irrespective of the expression system used.

Within the TGF beta superfamily the most common molecules used for bone regeneration come from the bone morphogenetic protein (BMP) family. Initially, BMPs were used as a cocktail of growth factors purified from bone. Urist et al., *Proc Natl Acad Sci U.S.A.*, 76, 1828-32 (1979). These mixtures were entrapped within a fibrin matrix and their therapeutic efficacy was measured. This provided an interesting preview of the therapeutic potential of fibrin mixed with BMP. However, the effects of each of the various growth factors present in the matrix were not determined.

BMP-2 and BMP-7 (OP-1), both have heparin binding affinity, are soluble at low pHs and are strong inducers of bone healing. Wozney J M, *Prog Growth Factor Res*, 1, 267-80 (1989); Wozney et al., *J Cell Sci Suppl*, 13, 149-56 (1990). rh-BMP-2 has demonstrated the greatest healing potential and is even able to induce bone formation at an ectopic site. Jin et. al., *J Biomed Mat Res*, 52, 841 (2000). Since the solubility of rh-BMP-2 at physiological conditions is low, it can precipitate within a matrix. Thus, this molecule fits the characteristics necessary for delivery.

The precipitation of this growth factor and thus its prolonged release has been further improved by using a recombinant form of rh-BMP-2, which is not glycosylated, and therefore is less soluble in fibrin or synthetic matrices. It is also possible to improve the precipitation of this growth factor when it is expressed in a glycosylated form by chemically or enzymatically deglycosylating it. The structural homology between the members of the BMP family is high; therefore, the results obtained with rh-BMP-2 can be expected to be obtained with the other BMPs, including BMP-7 (OP-1).

2. TGFβ Superfamily

The BMPs are themselves members of the transforming growth factor beta (TGFβ) superfamily, and the structural homology between the members of the TGFβ superfamily is also high. As such, results obtained with BMP-2 can be expected to be obtained with other members of the TGFβ superfamily and members of the cystine knot growth factor superfamily. The precipitation of growth factors that are members of the TGF☐ superfamily and their prolonged release is further improved by using recombinant forms that are not glycosylated and are therefore less soluble.

3. Deglylosylated BMPs

Deglycosylated versions of BMP and other growth factors can be obtained using a number of techniques. Several methods of deglycosylation are available in common practice, both chemical and biological. One chemical method occurs through the use of hydrogen fluoride. Briefly, glycosylated proteins are mixed with polyhydrogen fluoride, pyridine and a scavanger. This leads to essentially complete deglycosylation without modification of the protein itself. Biological methods center around the use of enzymes to cleave the glycosaminoglycans from the protein or expression in bacteria. Two examples are N-glycanase (Lin, Zhang et al. *J Neurochem*, 63, 758-768 (1994)) or glycopeptidase F (Chen and Gonatas *Biochem Biophys Res Commun*, 234, 68-72 (1997)), which can be used to deglycosylate proteins. These examples are merely illustrative of the biological and chemical methods that can be used to create a deglycosylated protein from an eukaryotic source (i.e. glycosylated), and are not a complete list of all possible methods. Using these standard techniques, the solubility of the glycosylated rh-BMP-2 can be made to mimic that of non-glycosylated rh-BMP-2. Furthermore, one can use excipients to reduce the solubility of proteins, e.g. polymers of opposite charge to reduce the net charge of the protein.

II. Methods of Incorporating Bioactive Molecules within the Matrix

Two primary methods for delivering bioactive factors are through biochemical and physical methods. In biochemical methods, matrices are created which have a chemical affinity for the bioactive factor of interest. When the matrix is mixed with the bioactive molecule, the release of the molecule can be delayed or eliminated. Physical methods, which may be used to retain the bioactive molecules in the matrix, include precipitation, co-precipitation, affinity precipitation, and physical entrapment. For example, in one embodiment, the bioactive molecules are precipitated inside a fibrin matrix to improve retention. This matrix, which contains the precipitated molecules, has a significant potential for wound healing.

A. Precipitation and Chemical Modification of Matrix

Precipitation can be combined with other retention methods to produce biomaterials which improve wound healing. One example is the use of modified biomaterials, which contain sites with binding affinity for bioactive molecules. The bioactive molecule is bound to the matrix, enhancing retention of the bioactive molecule in the matrix. For example, a matrix can be modified to include binding sites with heparin affinity and heparin can be added to bind with the matrix. Then, if the bioactive molecule has heparin binding affinity, the bioactive molecule will bind with the heparin and thus be retained in the matrix. This method can be performed in conjunction with the use of precipitation for slower release kinetics.

In one embodiment, the retention of rh-BMP-2 is enhanced by binding to heparin which is bound to a modified fibrin matrix. Thus deglycosylated rh-BMP-2 is retained in the matrix because it is precipitated within the matrix due to its poor solubility and bound to heparin due to its heparin binding affinity.

III. Methods of Using the Matrices to Enhance Wound Healing

A. Types of Patients in Need of Composition

These matrices provide a wide range of patients with therapies for healing bony defects. In one embodiment, the modified fibrin or synthetic matrices serve as a replacement for bone grafts, and thus may be applied in many of the same indications. These indications include, but are not limited to, spinal fusion cages, healing of non-union defects, bone augmentation, and dental regeneration. Additionally, in another embodiment, these matrices can be used in implant integration. In implant integration, implants can be coated with a modified matrix, either natural or synthetic, inducing the neighboring bone area to grow into the surface of the implant and preventing loosening and other associated problems. These examples are merely illustrative and do not limit the number of possible indications for which the matrices described herein can be used. In another embodiment, growth factor-enriched matrices can be used for healing chronic wounds in skin B. Methods of Administration In one embodiment, the material is applied to the wound area as a preformed matrix. In a second embodiment, the material is gelled in situ in the body. In both of these embodiments, the matrix material can be made from synthetic or natural precursor components.

The precursor components should not be combined or come into contact with each other under conditions that allow polymerization of the components prior to application of the mixture to the body. This is achieved by a system which separates the first precursor composition from the second precursor composition, where the first and second precursor compositions comprise components that form a three dimensional network upon mixing under conditions that allow polymerization of the components. Additionally at least one of the precursor compositions may contain a biologically active molecule which is a deglycosylated member of the cystine knot growth factor superfamily. Depending on the precursor components and their concentration, gelling can occur quasi-instantaneously after mixing. Therefore, it is difficult to inject a gelled material through an injection needle.

In one embodiment, the matrix is formed from fibrinogen. Fibrinogen, through a cascade of various reactions, gels to form a matrix when contacted with thrombin and a calcium source at appropriate temperature and pH. Therefore, during storage it is necessary to prevent the three components, fibrinogen, thrombin and a calcium source, from coming into contact with each other. As long as at least one of the three components is separate from the other two, the gel will not form. In one embodiment, fibrinogen, which may additionally contain aprotinin or another protease inhibitor to increase stability, is dissolved in a buffer solution at physiological pH, ranging from pH 6.5 to 8.0, preferably from pH 7.0 to 7.5, and stored separately from a solution of thrombin in a calcium chloride buffer (with a concentration range of 40 to 50 mM). The buffer solution for the fibrinogen can be a histidine buffer solution in a preferred concentration of 50 mM, which may additionally contain NaCl in a preferred concentration of 150 mM or Tris buffer saline, preferably at a concentration of 33 mM.

The bioactive molecule may be in either the fibrinogen or the thrombin solution. In a preferred embodiment, the fibrinogen solution contains the bioactive molecule. The fibrinogen and the thrombin solutions can optionally be stored frozen to enhance stability during storage. Prior to use, the frozen fibrinogen and the thrombin solutions are defrosted and mixed.

In another embodiment, fibrinogen and thrombin are stored together, but separately from the calcium source. In yet another embodiment, the fibrinogen is stored with the calcium source and separately from the thrombin.

In another preferred embodiment, fibrinogen and thrombin are stored in separate containers in lyophilized form. Either fibrinogen or thrombin can contain the bioactive molecule. Prior to use, a Tris or histidine buffer solution is added to the lyophilized fibrinogen. The buffer may additionally contain aprotinin. Prior to use, the lyophilized thrombin is dissolved in the calcium chloride solution. Then the fibrinogen and thrombin solutions are mixed. The mixing step preferably occurs by combining the separate containers, vials or syringes which contain each solution with a two-way connecting device having a needle attached at one side. In a preferred embodiment, the containers, vials or syringes are bipartite with two chambers separated by an adjustable partition. In the bipartite syringe containing fibrinogen, one of the chambers contains lyophilised fibrinogen, while the other chamber contains an appropriate buffer solution. If pressure is applied to one end of the syringe body, the partition moves and releases bulges in the syringe wall to transfer the buffer into the fibrinogen chamber and dissolve the fibrinogen. Similarly, a bipartite syringe body is used for storage and dissolution of the thrombin. Once both fibrinogen and thrombin are dissolved, both bipartite syringe bodies are attached to the two way connecting device and the contents are mixed by squeezing them through the injection needle attached to the connecting device. The connecting device may additionally comprise a static mixer to improve mixing of the contents.

In a preferred embodiment, the fibrinogen is diluted eight-fold and thrombin is diluted twenty-fold prior to mixing. This ratio results in a gelation time of approximately one minute.

In another preferred embodiment, the matrix is formed from synthetic precursor components capable of undergoing a Michael-type addition reaction. The nucleophilic precursor component (the multi-thiol) only reacts with the multi-acceptor component (e.g. a conjugated unsaturated group) at basic pH. Therefore, the three components which must be separated prior to mixing are the base, the nucleophilic component and the multi-acceptor component. Both the multi-acceptor and the multi-thiol component are stored as solutions in buffers. Both of the solutions can contain a cell attachment site and additionally a bioactive molecule. For example, the first solution of the system can contain the nucleophilic component and the second solution of the system can contain the multi-acceptor component. Either of the two solutions can contain the base; alternatively, the base can be present in both solutions. In another embodiment, the multi-acceptor and the multi-thiol can be mixed together in the first solution and the second composition can contain the base.

Connecting and mixing occurs in the same way as described above for fibrinogen. Similarly, the bipartite syringe body is equally well-suited for the synthetic precursor components as it is for the natural precursor components. However for the synthetic precursor components, the multi-acceptor and multi-thiol components are stored in pulverized form in one of the chambers and the basic buffer is in the second chamber.

C. Dosage

The matrices typically contain a dosage of 0.01 to 5 mg/mL of bioactive molecule. This dosage range is in accordance with the levels of active protein used in other clinical trials. However, lower doses may also be used due to the improved delivery that the matrices provide. For example, when non-glycosylated rh-BMP-2 was used in healing non-union cranial defects in rats, very low doses of 1-10 μg/mL were effective. As such, when using precipitated growth factors, and especially advantageous forms such as non-glycosylated forms, significant reductions in dosing are possible. Thus less bioactive molecule is necessary to get the same result.

The bioactive molecule is rleased completely within several weeks following administration. Within two to four weeks, it is likely that the original matrix has been completely remodeled and all of the bioactive molecules have been released.

The present invention can be further understood by reference to the following non-limiting examples.

EXAMPLE 1

Determination of Incorporation into Fibrin Gels

A test measuring the native enzymatic activity of the coagulation enzyme, factor XIIIa, was performed. This test was performed by measuring the ability of fibrin gel from two different sources to covalently incorporate a synthetic substrate during the coagulation process. One source of the fibrin gel came from a fibrin glue kit, while the second source came from a purified fibrin gel. Peptides derived from α2-plasmin inhibitor can be covalently incorporated into fibrin gels through the action of factor XIIIa. Thus, one method for testing the enzymatic activity in a fibrin gel or dilution thereof involves testing the ability of different fibrin sources to incorporate this same peptide. The gels were synthesized with various amounts of fluorescently labeled peptide and washed with TBS (0.03M, pH 7.4) to remove free peptide from the matrix. The gels were then degraded with the minimum amount of plasmin necessary and analyzed with size exclusion chromatography. The amount of fluorescent signal (i.e. peptide) bound to the matrix was determined when various dilutions of fibrin glue kits or purified fibrin gels were employed. This result was correlated to the amount of crosslinking activity present in the matrix.

Figure 1B:
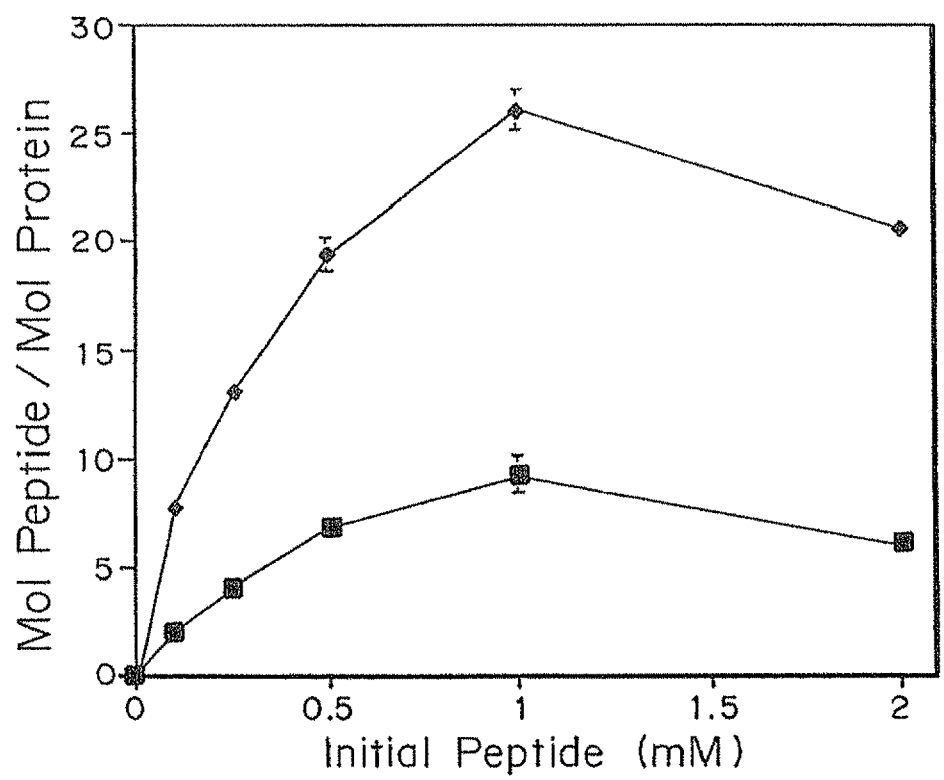

FIGS. 1A and 1B depict the results of this test. The results of the test demonstrate that when similar concentrations of fibrin are tested, the level of incorporation is similar. For example, the biochemical enzymatic activity in a fibrin glue kit (FIG. 1A) proved to be similar to that in a purified fibrin gel (FIG. 1B). However, higher protein (and factor XIIIa) concentrations lead to higher incorporation levels.

EXAMPLE 2

In Vivo Comparison of Fibrin Gels from Different Sources

A non-glycosylated recombinant form of a bone morphogenetic protein, which was prepared from prokaryotic cells (*E. coli*) (rh-BMP-2), was mixed in different fibrin gels, and the gels were tested in a rat femur defect. Because the protein was expressed in a prokaryotic system, it was not glycosylated. Fibrin gels were synthesized from a variety of sources. Purified fibrinogen from Sigma Chemical and a blood bank were employed, as well as fibrin glues (Baxter) at several dilutions. These gels were loaded with rh-BMP-2 and placed in a critical size (5 mm full thickness) femur defect. It was observed that all of the fibrin glue dilutions employed and the Sigma fibrin gave a similar healing response, leading to bridging of every critical size defect. The fibrin from the blood bank gave a lower overall response, which was more likely due to cell infiltration properties than to retention of the rh-BMP-2. Therefore, while the healing rate varied, the ability of the various matrices to retain rh-BMP-2 was not dependent on the exact fibrin matrix employed.

EXAMPLE 3

Comparison of Retention of Soluble and Insoluble Bioactive Molecules in a Fibrin Matrix This in vitro assay involved comparing the release kinetics of the entrapped non-glycosylated rh-BMP-2 to the release kinetics of a molecule that is known to have high solubility at physiological pH. Fibrin gels were polymerized using purified fibrinogen (Sigma) at 8 mg/mL and 2 U/mL thrombin at pH 7.4. Calcium was added so that the final concentration was 2.5 mM to increase the rate of gelation These gels were synthesized with a bioactive molecule present during the coagulation process and the retention of the molecule inside the fibrin matrix was determined. Gels were washed and kept in phosphate buffered saline (PBS 0.01M, pH 7.4) at 37° C. and the wash was changed every 12 hours. After thorough washing, the gels were degraded with 0.05 Units of plasmin. The amount of each bioactive molecule present in the washes and in the degraded matrix was determined.

Figure 2:
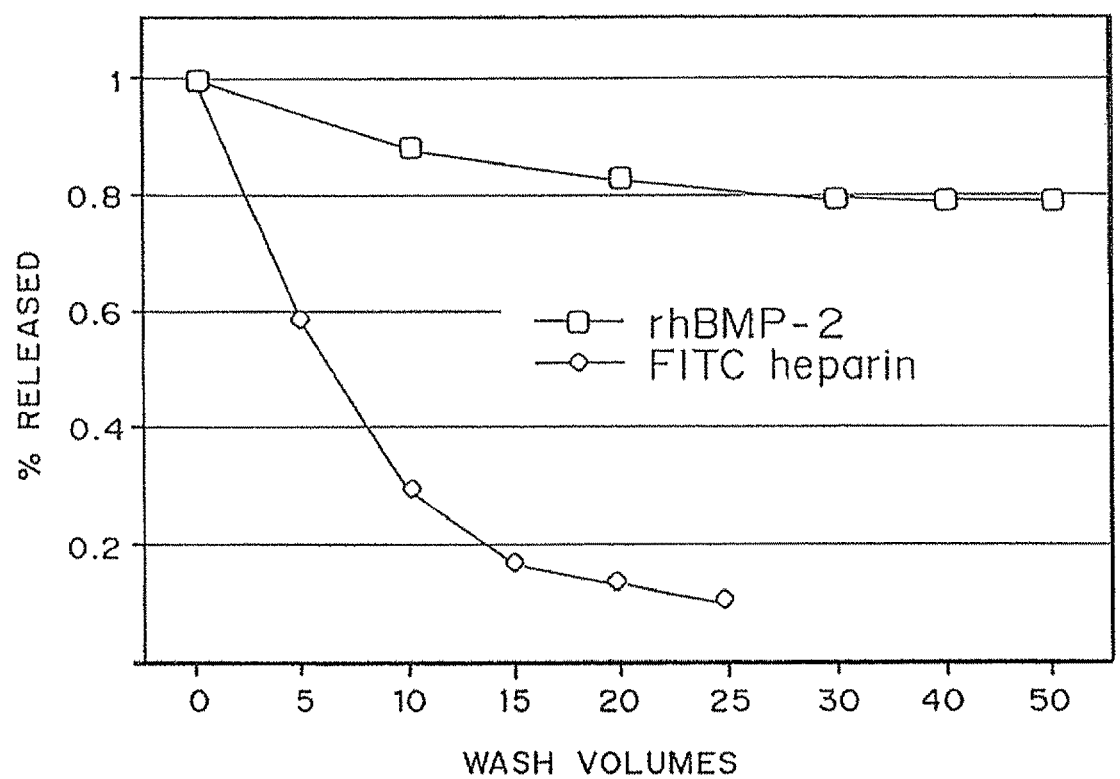
FIG. 2 is a graph measuring the retention of bioactive molecules in a fibrin matrix after washing. Two separate bioactive molecules, one water soluble molecule, heparin (◇), and one with low solubility at physiological pH, recombinant human bone morphogenetic protein (rh-BMP-2) (□), were added to the fibrin during polymerization and were repeatedly washed in phosphate buffered saline (PBS).

In the first test, the retention of FITC-labeled heparin, a highly soluble molecule, was tested. The amount of fluorescence in the washes and in the degraded gels was analyzed via fluorescence spectroscopy, and the percent of heparin released in each wash volume was determined. Fibrin gels contain a natural heparin binding sequence, therefore it was expected that there would be some retention of the heparin within the matrix. The fluorescence spectroscopy revealed that the release of heparin from the matrix was delayed relative to diffusion-controlled release (see FIG. 2). It is likely that this delay is due to the heparin binding site in fibrin. However, much of the heparin did diffuse out of the matrix, with essentially all of the heparin released from the matrix (see FIG. 2).

In the second test, non-glycosylated rh-BMP-2, a molecule with low solubility at pH 7.4, was trapped inside the fibrin matrix during polymerization. The release profile for rh-BMP-2 demonstrates that rh-BMP-2 was released from the matrix more slowly than FITC-labeled heparin. Further, about 80% of the initial dose remained precipitated inside the matrix at the completion of the test (see FIG. 2).

Figure 3A:
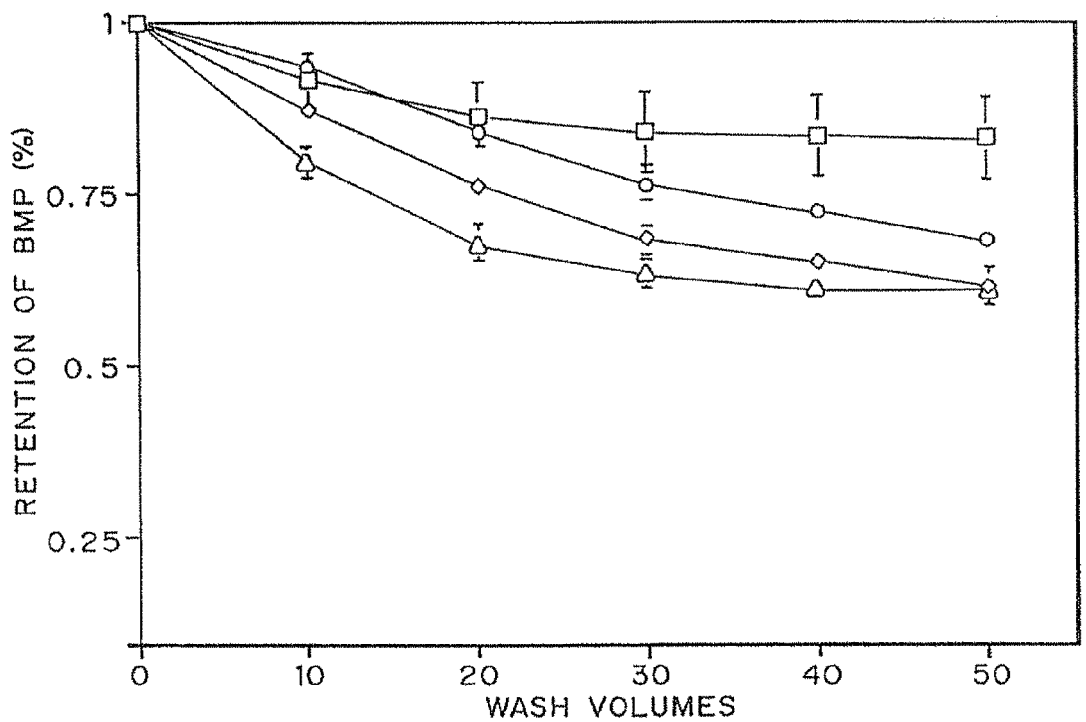
FIGS. 3A and 3B show the retention of rh-BMP-2 in fibrin gels.

A range of initial non-glycosylated rh-BMP-2 concentrations were tested, from 10 to 200 μg/mL. It can be seen that between 60 and 80% of the rh-BMP-2 remained in the gel even after 50 wash volumes (FIG. 3A). There is not a noticeable concentration dependence on the retention of rh-BMP-2, with high levels retained at all the relevant concentrations employed. Clearly then, this precipitation effect works at multiple concentrations of growth factor. This result is due to the low solubility of the non-glycosylated rh-BMP-2 at pH 7.4, which caused a significant amount of the rh-BMP-2 to precipitate inside the matrix. Thus, a physical mechanism, such as precipitation, can be used to entrap bioactive molecules within fibrin matrices.

Figure 3B:
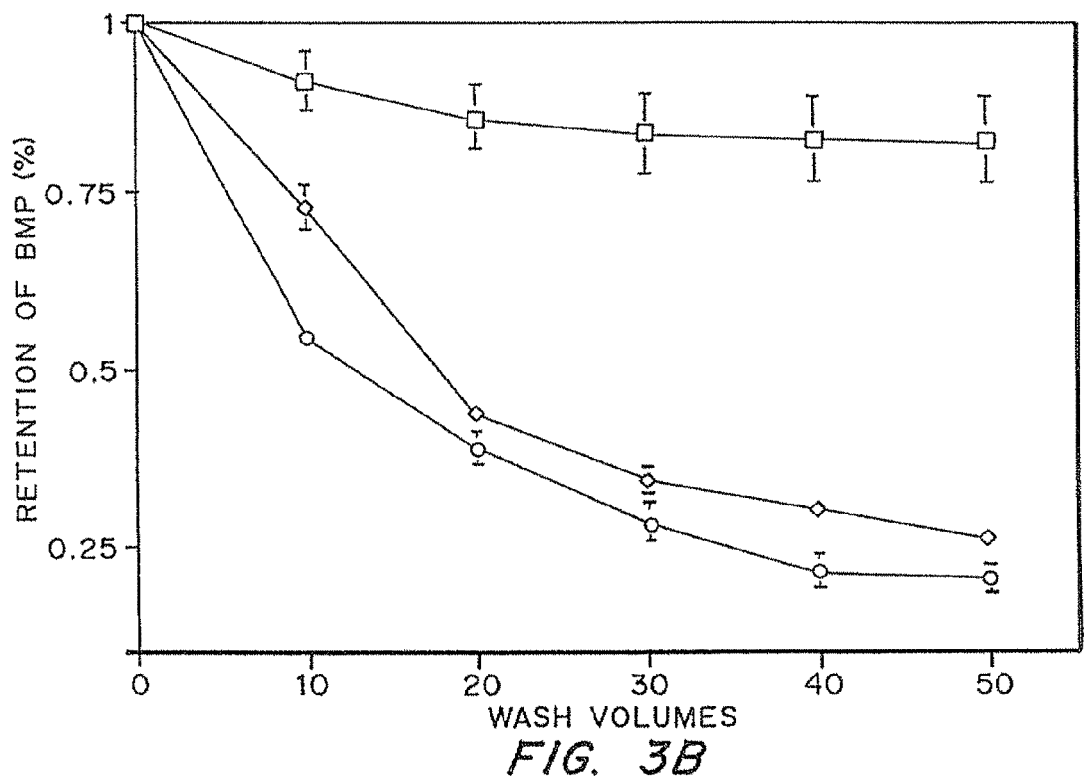

In order to test the mechanism for the high retention of non-glycosylated rh-BMP-2, retention of higher soluble species of rh-BMP-2 was studied. One possible method to improve the solubility of rh-BMP-2 is to link it with a highly soluble polysaccharide. This has been demonstrated previously with heparin, where it has been shown that the stability of proteins in solution can be enhanced when they are electrostatically bound to heparin. (Pineda-Lucena, Jimenez et al. *J Mol Biol,* 64, 162-178 (1996)) Alternatively, the polysaccharide can be covalently bound directly to the protein by using naturally (Rajah, Tsarbopoulos et al. *Biochem Biophys Res Commun,* 206, 694-702 (1995)) or synthetically (Tams, Vind et al. *Biochem Biophys Acta,* 1432, 214-221 (1999)) glycosylated versions. If the low solubility of rh-BMP-2 is the cause for its high retention, then both of these formulations should have a correspondingly lower retention. When heparin was premixed with rh-BMP-2 in a 1:1 molar ratio, the retention of rh-BMP-2 was demonstrated to be much lower, with only 20% being retained within the fibrin matrix (p<0.05). This was tested further by measuring the release of a glycosylated rh-BMP-2, derived from CHO cells. When the retention of this rh-BMP-2 was assessed, the release was very high, with only 30% remaining within the gel (FIG. 3B), an amount that is not statistically different from the result obtained with the mixture of prokaryotic rh-BMP-2 with heparin (FIG. 3A). Based on these results, it is likely that the mechanism by which prokaryotic rh-BMP-2 is retained at such high levels is through precipitation in the matrix. Thus, these results demonstrate the advantageous nature of non-glycosylated rh-BMP-2 within matrices, such as fibrin matrices, in the promotion of healing.

The results of Example 3 demonstrate the use of non-glycosylated rh-BMP-2 in bone regeneration in fibrin matrices. Non-glycosylated rh-EMP-2 will likewise be advantageous for regeneration of bone, as well as other tissues, in matrices other than fibrin. Moreover, the results of this Example may be extended by structural similarity to other members of the BMP family, and by the same structural similarity to other members of the TGF superfamily, including TGFβ1, TGFβ2, TGFβ3, and the numerous other members of the TGFβ superfamily. Furthermore, these results may also be extended to other wound healing situations, including healing of chronic wounds in the diabetic, in the venous insufficiency patient, and the pressure ulcer. In these and essentially all situations in promotion of healing and regeneration under the stimulatory influence of a growth factor, the prolonged presence of the growth factor in a regeneration matrix is desirable. As such, non-glycosylated members of the TGFβ superfamily are broadly useful in the promotion of wound healing and tissue regeneration.

EXAMPLE 4

In vivo Healing of a Critical Femur Defect in a Rat

Examples 4 and 5 describe in vivo tests, in which the bioactivity of the precipitated non-glycosylated rh-BMP-2 was examined. The in vivo assays used matrices with entrapped rh-BMP-2 in critical size bony defects in the rat. These defects do not spontaneously heal on their own. Therefore these models allow one to determine the osteogenic potential of a particular treatment. Schmitz J P, *Clin Orthop* 1986, 205, 299-308. Here, both a long bone model (5 mm full segmental femur defect) (Example 4) and a cranial model (8 mm defect) (Example 5) were employed. In each model, the healing potential of a fibrin matrix with rh-BMP-2 entrapped was compared to that for a fibrin matrix lacking rh-BMP-2.

Fibrin gels were polymerized using purified fibrinogen (Sigma) at 8 mg/mL and 2 U/mL thrombin at pH 7.4. Some of the gels included prokaryotic rh-BMP-2 mixed into the solution before gelation. Calcium was added to increase the rate of gelation.

Defects of 5 mm full-thickness were created in a rat femur and filled with fibrin matrices. Some matrices contained non-glycosylated rh-BMP-2 while others did not. For the matrices with rh-BMP-2, three different amounts of rh-BMP-2 were tested (2 μg, 5 μg, and 10 μg). The amount of regenerated bone within the defect was measured at four weeks to determine the efficacy of precipitated rh-BMP-2 in bone regeneration and compared to the results of the fibrin gels which lacked rh-BMP-2.

When the fibrin gels lacking rh-BMP-2 were explanted and tested at four weeks, the level of new, calcified bone within the defect margin was very low. Instead, the defect was bridged with fibrous tissue resulting in nonfunctional healing. None of the defects filled with a base matrix demonstrated complete healing.

At four weeks, fibrin gels with either 2, 5 or 10 μg of rh-BMP-2 added to the polymerization mixture were explanted and tested. Every animal that received either 5 or 10 μg of rh-BMP-2 in the defect exhibited complete healing, with the original defect filled with calcified bone and bone marrow and the entire gap bridged with calcified tissue. Animals that received materials with 2 μg of rh-BMP-2 in the defect healed very well as well, with 69% of the original defect area filled with mature, woven bone. The average percentage of bone defect area filled with calcified bone is shown in Table 1. In every sample, there was no sign of inflammation or scarring at the site of healing.

TABLE 1

Percent of Calcified Tissue in Healed Femur Defects

| Treatment | Regenerated Bone (%) |
|---|---|
| Fibrin | 7 |
| Fibrin + 2 μg rh-BMP-2 | 69 |
| Fibrin + 5 μg rh-BMP-2 | 100 |
| Fibrin + 10 μg rh-BMP-2 | 100 |

EXAMPLE 5

Healing the In vivo critical Cranial Defect

In Vivo Work with Fibrin Matrices

Fibrin gels were polymerized using purified fibrinogen (Sigma) at 8 mg/mL and 2 U/mL thrombin at pH 7.4. Some of the gels included prokaryotic rh-BMP-2 mixed into the solution before gelation. Calcium was added to increase the rate of gelation.

Defects of 8 mm were created in rat crania and filled with either a fibrin gel or a fibrin gel with rh-BMP-2 precipitated inside. For the matrices with deglycosylated rh-BMP-2, three different amounts of rh-BMP-2 were tested (1 μg, 5 μg, and 20 μg). The amount of regenerated bone within the defect was measured at three weeks to determine the efficacy of precipitated rh-BMP-2 in bone regeneration and compared to the results when fibrin gels were synthesized without rh-BMP-2 present.

At three weeks, the fibrin gels lacking rh-BMP-2 were explanted and tested. The level of new, woven bone within the defect margin was very low. The amount of new, woven bone within the defect was measured to be about 13% of the original defect area. None of the matrices led to complete healing of the defect, and most of the defect was still filled with fibrous tissue.

Figure 4A:
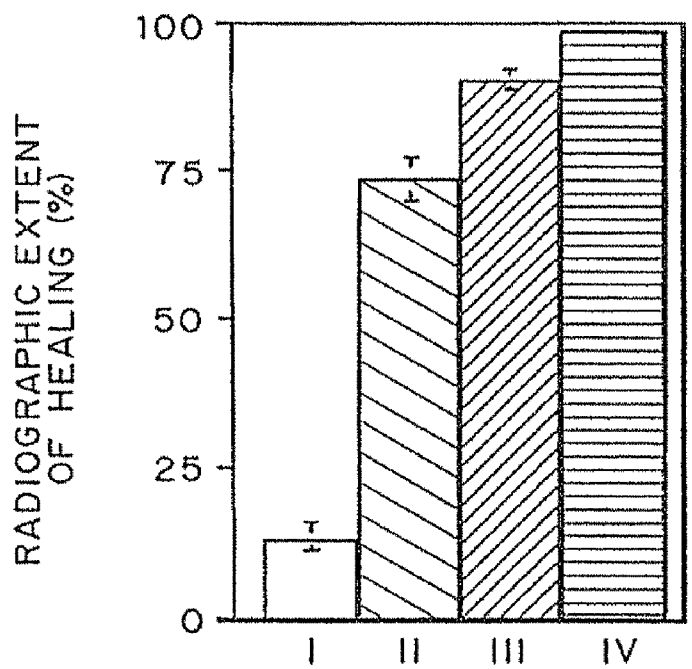
FIGS. 4A and 4B show healing levels of critical size rat calvarial defects. The healing efficacy of fibrin gels with various glycosylated and non-glycosylated rh-BMP-2 formulations mixed within the gel were measured.

Fibrin gels which contained rh-BMP-2, contained either 1, 5 or 20 μg of rh-BMP-2 added to the polymerization mixture. These materials were explanted and tested at three weeks. All of the defects treated with 20 μg of precipitated rh-BMP-2 were completely filled with woven bone and bone marrow (see FIG. 4A, column IV). The defects with 5 μg of rh-BMP-2 had nearly complete healing, with 90% of the original defect area filled with calcified tissue (see FIG. 4A, column III). The defects with 1 μg of rh-BMP-2 showed very good healing as well, with 73% of the defect area filled with new, woven bone (see FIG. 4A, column II). The average amount of the defect area filled with calcified tissue is shown in Table 2 and FIG. 4A. From Table 2, a dose dependence response is shown, with higher concentrations of precipitated rh-BMP-2 leading to better healing results. Finally, in every sample, there was no sign of inflammation or scarring at the site of healing or on the dura.

TABLE 2

Percent of Calcified Tissue in Healed Cranial Defects

| Treatment | Regenerated Bone (%) |
|---|---|
| Fibrin | 13 |
| Fibrin + 1 μg rh-BMP-2 | 73 |
| Fibrin + 5 μg rh-BMP-2 | 90 |
| Fibrin + 20 μg rh-BMP-2 | 100 |

Figure 4B:
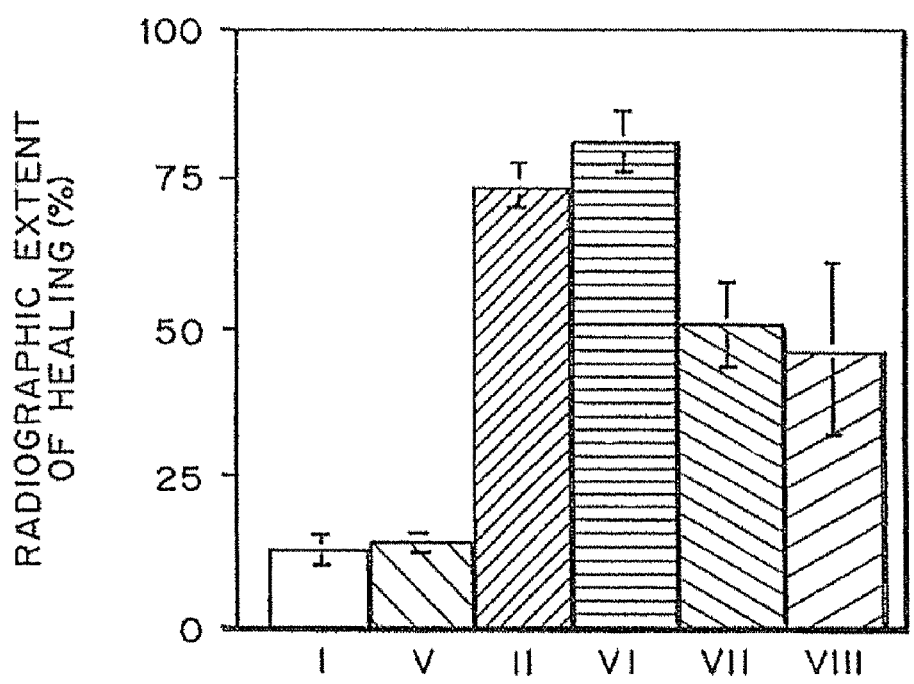

The two forms of rh-BMP-2 that had higher solubility were tested as well, and these had significantly lower healing responses. When 1 μg of non-glycosylated rh-BMP-2 was premixed with an equimolar amount of heparin and added before polymerization of a fibrin gel, the level of healing dropped to 50% (see FIG. 4B, column VII), statistically lower than the equivalent healing with 1 μg of rh-BMP-2 alone (73%) (see FIG. 4B, column II) ($p<0.05$). This result cannot be attributed to the effect of heparin alone because fibrin with heparin premixed within the matrix provided a similar healing response to that of fibrin alone (see FIG. 4B, columns I and V). Similarly, when glycosylated rh-BMP-2 was used, a lower healing response was achieved (see FIG. 4B, column VIII). Glycosylated rh-BMP-2 has a much higher specific activity than non-glycosylated rh-BMP-2, due to better folding, better dimerization and many other factors. However, when an equivalent molar dose (1 μg) of glycosylated rh-BMP-2 was employed, the healing response was still lower, with only 44% of the defect filled with calcified tissue, in comparison to the 73% result obtained with non-glycosylated rh-BMP-2 (see FIG. 4B).

As expected, using a plain fibrin matrix in the absence of any bioactive molecules to heal a critical size defect led to a very poor healing response, with little calcified tissue in either the femur or cranial model. This very low background healing with the control matrix demonstrates that the strong healing response that results when rh-BMP-2 is precipitated within the matrix represents a strong therapeutic healing ability in bony tissue. Therefore, physical processes, such as precipitation, especially through the use of a non-glycosylated TGFβ superfamily growth factor, provide a key tool for developing therapeutic matrices for wound healing.

In vivo Work with Synthetic Matrices

Enzymatically degradable synthetic matrices were tested in the same cranial defect model as the fibrin matrices described above. The synthetic gels were formed by reacting a four-armed PEG-vinylsulfone having a weight average molecular weight of 20 kDa with crosslinking linear peptides, such as GCRPQGIWGQDRC (SEQ ID NO:1), that contain multiple cystines at pH 7.5. The PEG-vinylsulfone was dissolved in a TEOA buffer (0.3 M, pH 8.0) to form a 10% (wt/wt) solution. The peptide was dissolved in the same buffer. The thiolates that were present reacted with the unsaturated moiety, giving an end crosslinked hydrogel. By incorporating degradation sequences between the two cystines that are specifically sensitive to either plasmin or collagenase, a synthetic substitute for fibrin and collagen (respectively) can be created. Through the addition of adhesion signals, usually RGD peptides, these gels can serve as a cell infiltration matrix and delivery matrix for bioactive molecules.

Synthetic gels as described above were created with 5 μg of deglycosylated rh-BMP-2 precipitated in the matrix and placed inside the 8mm critical size rat cranial defect. They were explanted after one, three and five weeks. No signs of inflammation or scar tissue were observed. Furthermore, the healing rate was 80% after five weeks, indicating that these synthetic matrices serve as suitable matrices for precipitation of deglycosylated rh-BMP-2 and act as healing matrices.

In vivo Work with Collagen Matrices

Clinically available adsorbable collagen sponges (Integra Lifesciences®) were obtained and cut into the appropriate shape for the rat critical size cranial defect. In order to prepare them for implantation, these sponges were then soaked in a solution containing 5 μg of non-glycosylated rh-BMP-2.

Defects of 8 mm were created in rat crania and a collagen sponge with rh-BMP-2 entrapped was placed inside the defect. The amount of regenerated bone within the defect at both three and five weeks was measured radiographically to determine the efficacy of precipitated non-glycosylated rh-BMP-2 in bone regeneration.

When the collagen sponges that contained 5 µg non-glycosylated rh-BMP-2 were explanted, there was no indication of an adverse reaction to the implanted material. In every sample, there was no sign of inflammation or scarring at the site of healing or on the dura. A total of seven samples were tested, with three tested at the 3 week time-point and four tested at the 5 week time-point. When samples were explanted at three weeks, each of the defects was completely filled with calcified tissue. After five weeks, a similar result was observed, where radiographically 94% of the defect was filled with woven bone. Clearly, the addition of non-glycosylated rh-BMP-2 to a collagen matrix provided excellent healing. This demonstrates that retention of non-glycosylated rh-BMP-2 within a matrix by utilization of a non-glycosylated form is also functional in collagen sponges.

EXAMPLE 6

Healing in the Canine Pancarpal Arthrodesis

The components for the gels were prepared such that the final concentration obtained were 8 mg/ml fibrinogen, 2.5 mM $Ca^{++}$, 10 NIH Units/ml of thrombin and 600 µg non-glycosylated rh-BMP-2/ml gel. Gelation began after mixing and injection of the components into the fracture site. Gelation time was 30-60 seconds. The contamination of the components with small amounts of blood in the wound did not influence the gelation properties.

Ten consecutive cases of client-owned dogs requiring a carpal panarthrodesis after a trauma were operated at the Small Animal Clinic of the University of Berne. The standard technique of dorsal plating was applied in all dogs. After reaming the joint cartilage, a plate of appropriate size was fixed with screws using the AO-technique. The operation field was than flushed with physiological NaCl-solution and the fibrin/non-glycosylated rh-BMP-2-solution was injected into the bone gaps (10-40 µg non-glycosylated rh-BMP-2/kg body weight). The gelation took 30-60 seconds to complete. The wound was closed routinely using absorbable suture material.

One dog (dog 10) suffered from a bilateral carpal injury after a fall. On both carpi, a panartrodesis was performed by the same blinded surgeon at the same day, and at the end of the procedure, the carpi were randomly selected to receive a spongiosa autotransplant or fibrin/non-glycosylated rh-BMP-2. While this case could not be included in the statistical analysis due to the bilateral injury, it did provide a direct internal comparison between autograft and fibrin/non-glycosylated rh-BMP-2.

After the postoperative radiographs, a protective splint was adapted. Limitation of free running and weekly bandage control was recommended for six weeks, as was performed in the control group. Standard control radiographs were taken at four, eight, and twelve weeks postoperatively. The dogs were clinically examined at the same time-points and their gait was evaluated. The radiographic bony healing was judged using a scoring system by an independent board certified radiologist (GS) and the results were compared to a control group of 17 dogs which were operated with the same technique but using a spongiosa autograft In the scoring system, 0 corresponded with no mineralized tissue in the joint gap visible, 1 corresponded with visible mineralized tissue in the joint gap, 2 corresponded with bony bridging of the joint gap, and 3 corresponded with remodeled bony bridging with absent subchondral plate.

No dog showed local or systhemic signs of adverse drug reactions, and the operation wounds consistently healed uneventfully. Only minor complications occurred in some patients related to the splint (small pressure wounds), which were managed by changing the bandage and cleaning the irritated skin.

Figure 5:
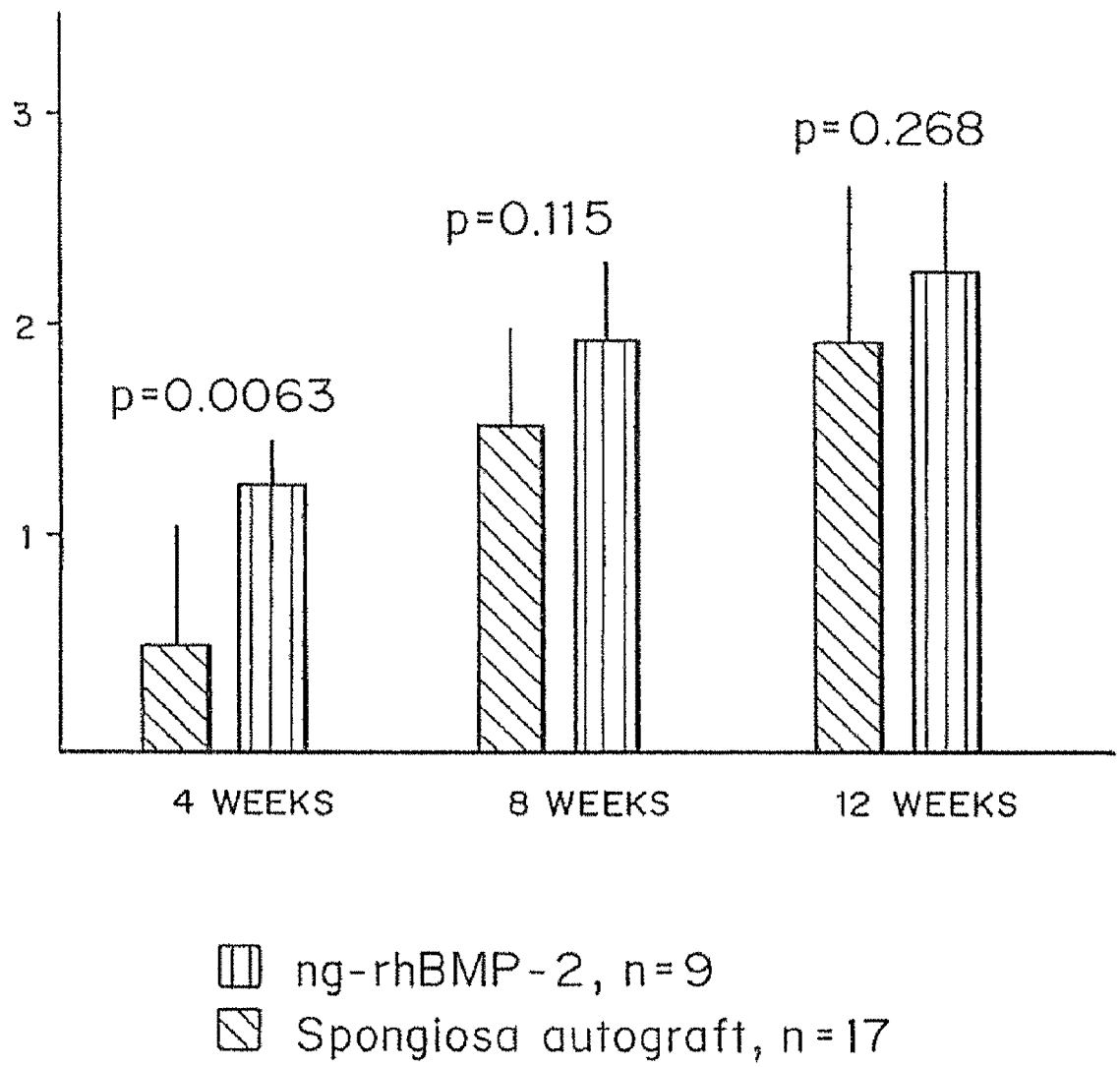
FIG. 5 is a bar graph of the radiologic healing of the canine pancarpal arthrodesis. The efficacy of using non-glycosylated rh-BMP-2 in fibrin matrices was tested in this defect and compared to the clinical standard of cancellous autograft (Spongiosa autograft). The mean of the healing scores obtained at four, eight and twelve weeks for the autograft and the non-glycosylated rh-BMP-2 in a fibrin gel were calculated. In the scoring system, 0 corresponded to no mineralization being visible, 1 corresponded to some mineralization being visible, 2 corresponded to a defect that is completely mineralized, and 3 corresponded to healed and remodeled defects. Nine dogs were used to test the non-glycosylated rh-BMP-2 in a fibrin gel and 17 dogs were used for the control, spongiosa autograft.

The mean radiologic healing score was at all time points (4, 8, 12 weeks) greater in the non-glycosylated rh-BMP-2 group than in the spongiosa group ($p_{4\ weeks}$=0.0063, $p_{8\ weeks}$=0.115, $p_{12\ weeks}$=0.268) (see FIG. 5). At 12 weeks post operative, 59% of the spongiosa group reached a score of 2 or greater in all joints (the standard level indicating clinical healing), whereas 87.5% of the non-glycosylated rh-BMP-2 group reached a score of 2 or greater.

Dog 10 with the bilateral panarthrodesis had a post operative period without complications. The first control radiograph after 4 weeks showed no visible difference in the bony healing of the two arthrodosis (score 1 for all joints). However, after eight weeks the spongiosa-treated carpus had no improvement (score 1), whereas the non-glycosylated rh-BMP-2 treated carpus improved to a score of 2. After twelve weeks, the score for the spongiosa treated leg was 2, and 2.33 for the non-glycosylated rh-BMP-2 treated arthrodesis.

The radiographs taken at later time-points demonstrated further healing and remodeling of the arthrodosis without forming bone outside the desired area, and no lysis or resorption of the induced bone was visible. No clinical problems developed in the operated animals in a post operative time range up to 14 months.

EXAMPLE 7

Healing in the Feline Long Bone Non-Union

The components for the gels were prepared such that the final concentration obtained were 8 mg/ml fibrinogen, 2.5 mM $Ca^{++}$, 10 NIH Units/ml of thrombin and 600 µg non-glycosylated rh-BMP-2/ml gel. Gelation was allowed after mixing and injection of the components into the fracture site. Gelation time was 30-60 seconds. The contamination of the components with small amounts of blood in the wound did not influence the gelation properties.

Five consecutive cases of fracture nonunions in client-owned short hair cats, 3 male and 2 female with the mean age of 3.4 years (2 to 10 years), were treated at the Veterinary Teaching Hospital of the University of Berne. Each patient had an atrophic nonunion, that showed no progression in healing for a minimum of three months before they were treated with non-glycosylated rh-BMP-2. Primary fixation of the fractures were provided by an external fixator in cats #1-4 and im-pinning in cat #5. In cats #1-3 and 5 the primary fixation was unstable, and a plate was applied to gain stability. In the same operation the non-glycosylated rh-BMP-2 was inserted to the fracture site. In cat #4, the external fixator showed no signs of loosening and the non-glycosylated rh-BMP-2 was inserted through a stab incision to the fracture gap (see Table 3). Two months after application of the non-glycosylated rh-BMP-2, the plate loosened in cat #3 because of a fall. The plate was removed and 300 µg non-glycosylated rh-BMP-2 in fibrin was inserted a second time to the fracture area. A cast was added and after six weeks, and an im-pin was inserted to provide stability. In cat #5, a mini plate was placed on the lateral aspect of the metacarpal bone (Mc) 5 to stabilize the fractures together with the intact Mcg. Through a small approach to the fractures of the Mc 3 and 4, fibrin with 300 µg non-glycosylated rh-BMP-2 was injected.

Several control radiographs were taken in all cases during the months following the treatment with fibrin and non-glycosylated rh-BMP-2. No cat showed local or systemic signs of adverse drug reactions, the operation wounds healed uneventfully.

TABLE 3

Healing in the Feline Non-union

| Cat # | Fracture | Time | Treatment | Result |
|---|---|---|---|---|
| 1 | R/U prox. | 3 month | Plate, 1x BMP | Healed |
| 2 | R/U dist. | 12 month | Plate, 1x BMP | Healed |
| 3 | Tibia | 12 month | Plate, 1x BMP Cast, 1x BMP im-pin | Healed |
| 4 | Tibia | 4 month | 1x BMP (ExFix) | Healed |
| 5 | Mc 3, 4, 5 | 5 month | Plate, 1x BMP | Not Healed |

In cat #1, four weeks after treatment new calcified tissue was visible on the radiographs in the fracture area. Four months after the application of the non-glycosylated rh-BMP-2 the fracture was healed, and the cat showed no lameness.

In cat #2, the fracture gap after the placement of a mini-T-plate was small, and six weeks after the treatment with non-glycosylated rh-BMP-2, the fracture was bridged with excellent limb function.

Cat #3 suffered a very comminuted tibial fracture, which was stabilized by an external fixateur. The tibia developed an atrophic nonunion with severe bone loss. A 2.7 mm-plate was applied after shortening of the fibula to reduce the gap of the tibia. The bone from the fibula was morselised and mixed in the fibrin with the non-glycosylated rh-BMP-2 to provide living cells to the fracture site. The follow-up radiographs showed new bone formation and building up of a new cortex along the whole tibia. After the pull out of the distal screws because of a trauma, the plate was removed, and 300 μg non-glycosylated rh-BMP-2 in fibrin was applied a second time. The bone continued to augment, and six months after the first non-glycosylated rh-BMP-2 treatment, the fracture had healed.

Cat #4 had an open tibial fracture, which was stabilized by an external fixateur. After a mild, transient osteomyelitis, the bone of the tibia started to atrophy despite the stable conditions. The fibrin/non-glycosylated rh-BMP-2 was applied through a stab incision in the fracture gap. After four weeks, no bony reaction was visible on the radiographs, but after seven weeks the fracture gap was smaller, and 4 months after the treatment the bone had bridged.

In cat #5, the metatarsal bones 3, 4 and 5 severely atrophied after the stabilization of comminuted fractures with im-pinning. The control radiographs revealed no effect of the non-glycosylated rh-BMP-2 after four and seven weeks. The owner denied further treatment, no longer follow up was possible.

EXAMPLE 8

Rentention of Non-glycosylated rh-PDGF-AB in Fibrin and Synthetic Matrix

An in vitro assay assessed the retention of non-glycosylated rh-PDGF-AB in fibrin and a synthetic matrix. PDGF-AB is known to contain a N-glycosylation site on the A chain, which is suggested to be used when the protein is expressed by a eukaryotic cell. rh-PDGF-AB expressed in *E. coli*, which is expected to be non-glycosylated, was used in this study, and is soluble in physiological pH up to 0.2 mg/mL. (Hoppe, J. et al, *Biochemistry*, 28, 2956-60 (1989); Hoppe, J. et al. *Eur J Biochem*, 187, 207-14 (1990))

Non-glycosylated PDGF-AB was tested at 2 μg in 50 μL of gel. Fibrin gels were polymerised using a modified formulation of TISSUCOL™ Kits (Baxter) (a fibrin sealant containing fibrinogen, aprotinin, thrombin, and $CaCl_2$), and the synthetic gel was formed of 4-armed PEG-acrylate cross-linked with 2-armed PEG-thiol. The gels were washed in buffered saline (PBS 0.01 M, pH 7.4, with 0.1% BSA), and the wash was changed after 12 hours. The amount of therapeutic molecules released in the wash was then determined by ELISA.

After 20 wash volumes, 0.7 μg of protein was detected in the wash buffer of the fibrin matrix, which indicates a retention of 65% total protein load in the fibrin matrix. In the synthetic matrix, less than 4 ng was released after 20 wash volumes, as no protein was detected within the sensitivity of the assay, suggesting full retention of the protein load. As control against interference of matrix in the assay or degradation of the protein, spiked samples were tested and results showed that a significant amount of protein was detectable after 20 wash volumes. Based on these results, it is shown that prokaryotic rh-PDGF-AB can be retained within matrices, such as fibrin and synthetic PEG-gels, to be used in the promotion of healing applications.

It is understood that the disclosed invention is not limited to the particular methodology, protocols, and reagents described herein. Further, the terminology used herein is for the purpose of describing particular embodiments, and is not intended to limit the scope of the present invention.

Those skilled in the art will recognize, or be able to ascertain using no more than routine experimentation, many equivalents to the specific embodiments of the invention described herein. Such equivalents are intended to be encompassed by the following claims.

We claim:

1. A method for improving healing of bony defect sites in a patient at a bony defect site in need thereof comprising
    administering to the site a composition consisting of
    a fibrin matrix, and
    a non-glycosylated TGFβ superfamily growth factor that is capable of being glycosylated,
    wherein the non-glycosylated growth factor is precipitated in the matrix in an effective amount to enhance healing of bony defects,
    wherein the growth factor enhances healing of bony defects at the site.

2. The method of claim 1 wherein the growth factor is a member of the bone morphogenic protein family.

3. The method of claim 2, wherein the growth factor is selected from the group consisting of rh-BMP-2 and rh-BMP-7.

4. The method of claim 3, wherein the growth factor is rh-BMP-2.

5. The method of claim 1, wherein the site is selected from the group consisting of treatment sites containing spinal fusion cages, bone augmentation sites, dental regeneration sites, and bone regeneration sites following trauma.

6. The method of claim 1, wherein at least 60% of the growth factor is retained in the matrix after 10 wash volumes.

7. The method of claim 1, wherein the growth factor is released to the site for up to four weeks following administration.

8. The method of claim 7, wherein the growth factor is released to the site for two to four weeks following administration.

9. A method for improving healing of bony defect sites in a patient at a bony defect site in need thereof comprising
    administering to the site a composition consisting of a first and a second precursor component required to form a fibrin matrix, and a non-glycosylated TGFβ superfamily growth factor that is capable of being glycosylated,
    wherein at least one of the precursor components contains the non-glycosylated growth factor,
    wherein the first and the second precursor components mix to form the matrix,
    wherein first precursor component contains fibrinogen and the second precursor component contains thrombin,
    wherein the non-glycosylated growth factor is precipitated in the matrix in an effective amount to enhance healing of bony defects, and
    wherein the growth factor enhances healing of bony defects at the site.

10. The method of claim 9, wherein the site is selected from the group consisting of treatment sites containing spinal fusion cages, bone augmentation sites, dental regeneration sites, and bone regeneration sites following trauma.

11. The method of claim 9, wherein the composition is administered to the site by injection.

12. The method of claim 9, wherein the growth factor is a member of the bone morphogenic protein family.

13. The method of claim 12, wherein the growth factor is selected from the group consisting of rh-BMP-2 and rh-BMP-7.

14. The method of claim 13, wherein the growth factor is rh-BMP-2.

* * * * *

UNITED STATES PATENT AND TRADEMARK OFFICE
CERTIFICATE OF CORRECTION

PATENT NO. : 8,309,518 B2  
APPLICATION NO. : 12/845354  
DATED : November 13, 2012  
INVENTOR(S) : Jason C. Schense et al.

Page 1 of 1

It is certified that error appears in the above-identified patent and that said Letters Patent is hereby corrected as shown below:

Column 2, line 24, replace "biologically" with --biological--.  
Column 3, line 59, replace "hereing" with --herein--.  
Column 4, line 5, replace "glycosolated" with --glycosylated--.  
Column 4, line 12, replace "polysaccaride" with --polysaccharide--.  
Column 4, line 12, replace "has been" with --have been--.  
Column 6, line 66, replace "cystine" with --cysteine--.  
Column 6, line 67, replace "cystine" with --cysteine--.  
Column 7, line 1, replace "cystines" with --cysteines--.  
Column 7, lines 61-62, replace "cystines" with --cysteines--.  
Column 7, line 63, replace "Cystines" with --Cysteines--.  
Column 8, line 50, replace "TGF□" with --TGFβ--.  
Column 8, line 53, replace "Deglylosylated" with --Deglycosylated--.  
Column 8, line 60, replace "scavanger" with --scavenger--.  
Column 9, line 2, replace "from an" with --from a--.  
Column 9, line 63, insert a --.-- after the term "skin".  
Column 11, line 48, replace "rleased" with --released--.  
Column 12, line 21, replace "lead to" with --led to--.  
Column 12, line 58, insert a --.-- after the term "gelation".  
Column 16, line 40, replace "cystines" with --cysteines--.  
Column 16, line 45, replace "cystines" with --cysteines--.  
Column 17, line 25, replace "concentration" with --concentrations--.  
Column 17, line 62, insert a --.-- after the term "autograft".  
Column 18, line 1, replace "systhemic" with --systemic--.  
Column 18, line 37, replace "concentration" with --concentrations--.  
Column 18, line 51, replace "were provided" with --was provided--.  
Column 20, line 8, replace "Rentention" with --Retention--.  
Column 20, line 13, replace "a N-glycosylation site" with --an N-glycosylation site--.

Claim 9, column 22, line 18, replace "wherein first precursor" with --wherein the first precursor--.

Signed and Sealed this  
Nineteenth Day of March, 2013

Teresa Stanek Rea  
*Acting Director of the United States Patent and Trademark Office*

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Crosslinking linear peptide with multiple cysteins

```
<400> SEQUENCE: 1

Gly Cys Arg Pro Gln Gly Ile Trp Gly Gln Asp Arg Cys
1               5                   10
```